(12) United States Patent
Schauerte

(10) Patent No.: US 6,611,713 B2
(45) Date of Patent: Aug. 26, 2003

(54) IMPLANTABLE DEVICE FOR DIAGNOSING AND DISTINGUISHING SUPRAVENTRICULAR AND VENTRICULAR TACHYCARDIAS

(76) Inventor: Patrick Schauerte, Moeschepfad 16, D-52134 Herzogenrath (DE)

( * ) Notice: Subject to any disclaimer, the term of this patent is extended or adjusted under 35 U.S.C. 154(b) by 31 days.

(21) Appl. No.: 09/726,500

(22) Filed: Nov. 30, 2000

(65) Prior Publication Data
US 2002/0035335 A1 Mar. 21, 2002

(30) Foreign Application Priority Data
Nov. 30, 1999 (DE) ......................... 199 57 648

(51) Int. Cl.⁷ ............................................... A61N 1/362
(52) U.S. Cl. .............................................. 607/14; 607/5
(58) Field of Search ..................... 607/5, 14; 600/518

(56) References Cited
U.S. PATENT DOCUMENTS
5,507,784 A * 4/1996 Hill et al. ................... 607/14

* cited by examiner

Primary Examiner—Jeffrey R. Jastrzab
(74) Attorney, Agent, or Firm—Hahn Loeser + Parks LLP; Stephen L. Grant

(57) ABSTRACT

An implantable device for diagnosing and distinguishing supraventricular and ventricular tachycardias includes electrodes for stimulating parasympathetic nerves of the atrioventricular and/or sinus node; electrodes for stimulating the atria and ventricles and/or for ventricular cardioversion/defibrillation; a device for producing electrical parasympathetic stimulation pulses passed to the electrodes; a device for detecting the atrial and/or ventricular rate, by ascertaining a time interval between atrial and/or ventricular depolarization; a device for programming a frequency limit above which a rate of the ventricles is recognized as tachycardia; a comparison device for comparing the measured heart rate during parasympathetic stimulation to the heart rate prior to or without parasympathetic stimulation and/or to the frequency limit, which delivers an output signal when with parasympathetic stimulation the heart rate falls below the comparison value by more than a predetermined amount; and an inhibition unit which responds to the output signal to inhibit ventricular myocardial over-stimulation therapy.

19 Claims, 4 Drawing Sheets

Figure 1A:
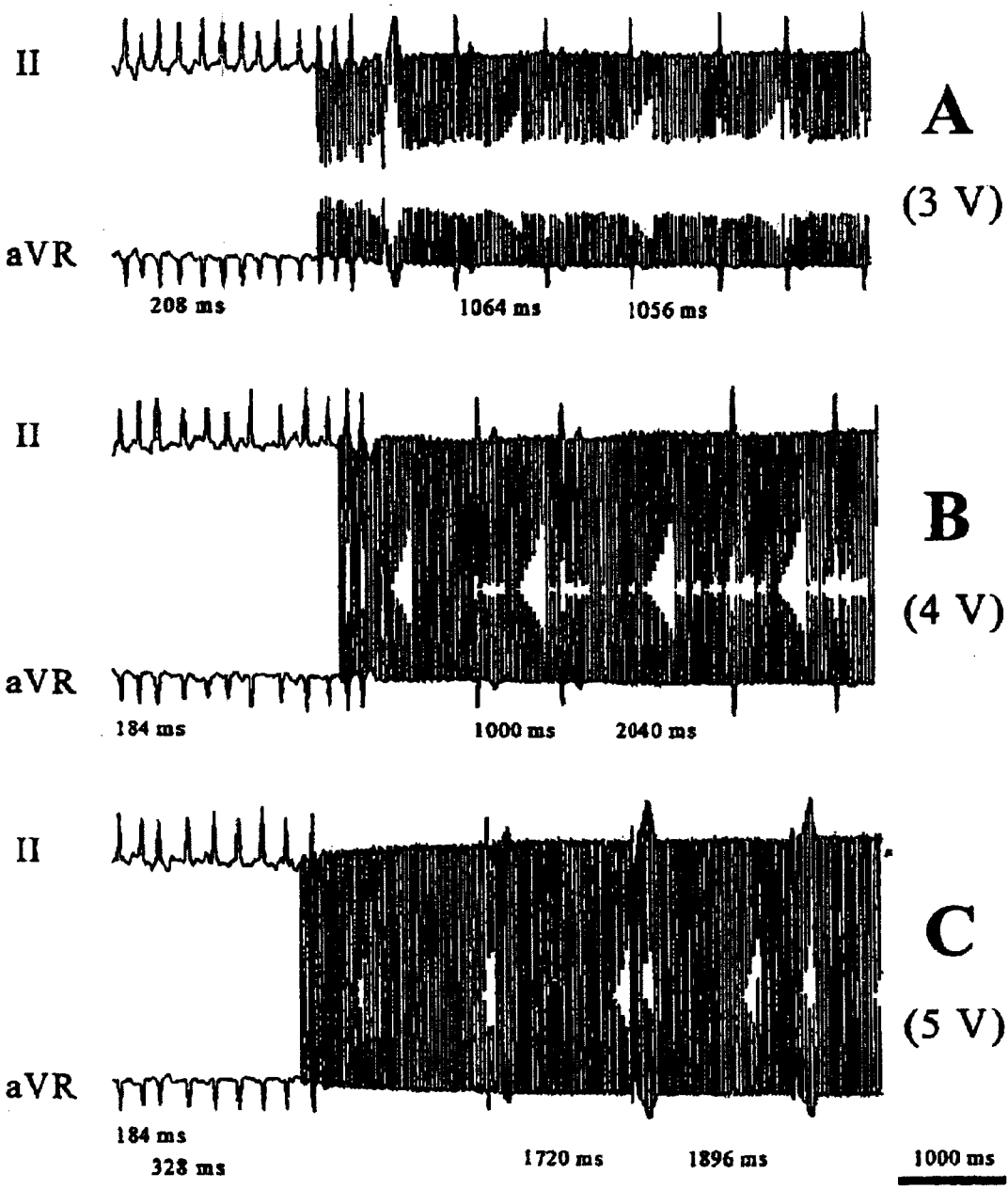
Figure 13:
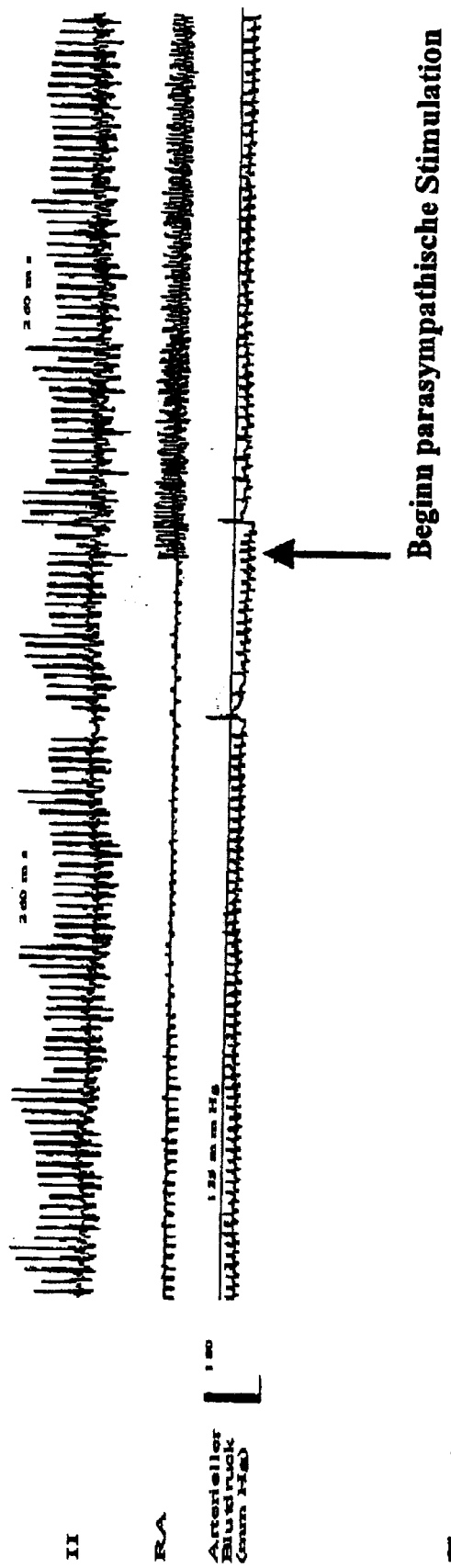

IMPLANTABLE DEVICE FOR DIAGNOSING AND DISTINGUISHING SUPRAVENTRICULAR AND VENTRICULAR TACHYCARDIAS

The invention concerns an implantable device for diagnosing and distinguishing supraventricular and ventricular tachycardias.

In a healthy human, a rhythmic cardiac action is predetermined by a natural pacemaker in the so-called sinus node. That electrical pulse is passed by way of the atria of the heart to the atrioventricular node, by way of which excitation of the main chambers or ventricles of the heart is implemented. A rise in the heart rate of over 100 beats per minute is referred to as tachycardia. Under conditions of physical stress, there is a rise in the sinus node frequency which is transmitted by way of the atrioventricular node to the ventricles (sinus tachycardia). In many humans there is no sinus rhythm but the atria are excited electrically quickly and regularly (atrial tachycardia) or completely irregularly and quickly (so-called atrial fibrillation=AF). That situation can involve very fast transmission of the electrical atrial pulses to the ventricles. AF is the most frequent disturbance in cardiac rhythm in a human being. AF occurs with increasing age and is to be encountered in about 4% of people who are over 60 years old and 10% of people who are over 75 years old. Besides these so-called "benign" (atrial) tachycardias which cannot result in cardiac arrest, there are also so-called "malign" tachycardias which have their origin primarily in the ventricles and which are in part transmitted in retrograde fashion by way of the atrioventricular node to the atria. By virtue of the contraction movements of the ventricles in the event of ventricular tachycardia, which are generally more adverse in contrast to atrial tachycardia, a loss of consciousness of the patient generally occurs quickly in situations involving ventricular tachycardias, or the ventricular tachycardia degenerates into ventricular fibrillation, which amounts to functional cardiac arrest. Ventricular tachycardias or ventricle fibrillation are also the cause of so-called sudden cardiac death which at the present time is the leading cause of death in the industrialized countries.

Implantable cardioverter/defibrillators (ICD) can automatically terminate ventricle frequencies (ventricular tachycardias or ventricle fibrillation) which are life-threateningly fast, by virtue of ventricular over-stimulation or cardioversion/defibrillation. It could be shown that ICDs result in a significant prolongation of the survival rate of patients after having suffered a cardiovascular arrest and are in that respect clearly superior to drug therapy. Furthermore, ICDs also extend the life expectancy in the case of patients with restricted ventricular pump function (primary prophylaxis). The therapy (shock) delivery of ICDs occurs when the ventricle frequency exceeds a programmed limit value. In that respect, no consideration is initially given to whether the fast ventricle frequency is caused by a "benign" rise in the frequency of the atrias, which is not life-threatening (sinus tachycardias, atrial tachycardias or atrial fibrillation), or a life-threatening rise in the frequency of the ventricles. Therefore, many patients in which an ICD was implanted involve inadequate shock delivery in a situation involving supraventricular tachycardias.

Therefore, besides frequency, various ICDs evaluate additional criteria which is intended to make it possible to distinguish supraventricular from ventricular tachycardias. Thus, many but not all supraventricular tachycardias are distinguished by a gradual rise in the heart rate at the beginning of the tachycardia. By measurement of the sudden jump in rate at the beginning of a tachycardia, it is classified then as supraventricular or ventricular and in the case of a supraventricular tachycardia the ICD shock therapy is suppressed. Another criterion involves evaluating the interval stability of consecutive ventricle beats and therefore distinguishes between irregular tachycardias (AF) and regular tachycardias (atrial tachycardias, sinus tachycardias, ventricular tachycardias). As the morphology of the intracardial ECG at the ventricle electrode of the ICDs also differs in situations involving supraventricular and ventricular tachycardias, a morphology criterion is also implemented to distinguish supraventricular and ventricular tachycardias, in many ICDs. Finally, additional atrial electrodes are also connected to ICDs. Besides the atrial frequency, those electrodes can also measure the ventricle frequency and contribute to better distinguishing supraventricular and ventricular tachycardias. Thus, with an atrial frequency which is faster than the ventricle frequency, a supraventricular tachycardia is assumed to apply, and vice-versa. However the two-chamber criteria fail in the case of patients with chronic atrial fibrillation or often also in the case of atrial palpitation with 2:1 atrioventricular transmission as frequently an atrial excitation falls into the post ventricular atrial refractory time. The two-chamber criterion frequently also fails in the case of ventricular tachycardias with 1:1 retrograde conduction. In summary the stated criteria for distinguishing supraventricular and ventricular tachycardias are distinguished by moderate sensitivity and specificity in regard to the detection of a supraventricular tachycardia. When a supraventricular tachycardia situation is detected on the basis of the described criteria therefore the ICDs withhold a shock delivery only for a short time in order to permit spontaneous termination of the probably supraventricular tachycardia. By virtue of the low level of sensitivity and specificity however, in the event of absence of tachycardia termination, cardioversion shocks are then still delivered after some seconds to minutes. As in the case of supraventricular tachycardias cardioversion shocks frequently do not terminate the tachycardia, multiple shocks (up to 5–6) are then delivered when the patient is conscious, which is very painful for the patient. In addition, the unnecessary supply of shocks can give rise to premature exhaustion of the battery of the units. Besides the shock therapy, ICDs can also produce so-called over-stimulation therapies in the ventricles. If an over-stimulation therapy is erroneously afforded in a situation involving supraventricular tachycardias, that can give rise to triggering of life-endangering ventricular tachycardias.

The parasympathetic autonomous nerve system projects nerve fibers by way of the vagus nerve onto groups of nerve cells which are disposed on or in the heart and the adjoining large vessels. Larger groups of those nerve cells are embedded in fatty tissue and are visible as so-called "fat pads" on the exterior of the heart. Three prominent "fat pads" have been described:

One fat pad at the boundary of the upper right pulmonary valve, the superior vena cava and the right atrium projects predominantly parasympathetic fibers onto the sinus node. Epicardial electrical stimulation of that fat pad at 20 Hz reduces the frequency of the sinus node in dogs.

A further fat pad is disposed at the boundary of the left atrium, the inferior vena cava and the entrance of the coronary sinus. Epicardial electrical simulation in dogs resulted in a marked fall in the ventricle frequency in an AF situation or complete atrioventricular block.

Another fat pad was described between the base of the aorta, the right pulmonary artery and the superior vena cava.

Extravascular simulation of that fat pad resulted both in a slowing of the sinus node frequency and also a slowing of atrioventricular transmission.

In addition, it was also possible in dogs to achieve a reduction in the sinus node frequency and also a reduction in the speed of atrioventricular transmission by extravascular electrical stimulation of parasympathetic cardiac nerve fibers which extend along the superior venae cavae to the sinus and atrioventricular nodes.

An apparatus and a method of distinguishing ventricular and supraventricular tachycardias is known from U.S. Pat. No. 5,243,980. A disadvantage in that respect is that the known apparatus also provides that a defibrillation cycle is initiated in situations involving supraventricular tachycardias. That however is harmful to the patient.

The invention is based on the realization that any stressing defibrillation is prevented in the case of a supraventricular tachycardia, so that the operating life of the energy sources is also increased, which ultimately is also to the benefit of the patient as unnecessary premature re-implantation procedures are avoided.

In accordance with the present invention a medical electrostimulation device for diagnosing and distinguishing supraventricular and ventricular tachycardias is provided, comprising electrodes for the electrical stimulation of parasympathetic nerves which innervate the atrioventricular and/or sinus node;

electrodes for the electrical stimulation of the atria and ventricles and for ventricular cardioversion/defibrillation;

a device for producing electrical stimulation pulses which are passed to the electrodes;

a device for detecting the rate at which the human atria and ventricles beat, wherein said device measures ventricular and atrial electrical depolarization;

a device for programming a frequency limit above which a heart rate of the ventricles is recognized as tachycardia; and a start unit which reacts to the detection unit and which activates the stimulation pulse-producing device when the detected heart beat rate of the ventricles exceeds the programmed frequency limit, wherein when the presence of a supraventricular tachycardia is ascertained, by stimulation of the fat pads, triggering of a defibrillation operation is prevented.

Those measures reliably prevent the triggering of unnecessary defibrillation steps which often only trigger off fibrillation phenomena which are life-endangering for the patient.

The stimulation pulses can be delivered over a defined period continuously or in the form of short bursts. Stimulation bursts in turn can be delivered either asynchronously or in synchronized relationship with the atrial or ventricular depolarization.

Synchronization of the bursts is then effected with a varying time delay in relation to the measured atrial/ventricle depolarization in the atrial/ventricle refractory time.

The device further includes a unit which compares the ventricle frequency measured during stimulation by the detection unit with the ventricle frequency before/without stimulation and the frequency limit;

a start/inhibition unit which is responsive to the comparison unit and which restrains ventricular myocardial over-stimulation therapy and/or cardioversion/defibrillation therapy; and a stimulation unit which can provide atrial and/or ventricular electrical myocardial stimulation or cardioversion/defibrillation.

In the case of patients with the simultaneous occurrence of sinus tachycardias and atrial tachycardias/atrial fibrillation the electrodes for stimulation of the parasympathetic nerves which innervate the sinus node/atrium and atrioventricular node can be placed in the superior vena cava after the mouth opening of the left vena anonyma or in the left/right vena anonyma. Alternatively, placement can also be in the pulmonary artery (stimulation of the so-called third parasympathetic fat pad). In the case of patients who, besides ventricular tachycardias, predominantly suffer atrial tachycardias/atrial fibrillation, the parasympathetic stimulation electrodes can be placed in the posterior-inferior right atrium or at the ostium or in the proximal coronary sinus.

The stimulation electrodes can be secured endocardially or epicardially to the above-mentioned stimulation locations. Nerve stimulation can be implemented in unipolar or bipolar mode, in which respect the bipolar reference electrode can be part of the nerve stimulation probe or part of a second nerve stimulation probe which is implanted in the proximity of the first nerve stimulation electrode. In this respect, fixing of the electrodes can be effected actively, for example by screw mechanisms, or passively, for example by anchoring devices.

The pulse-producing unit for the stimulation of parasympathetic nerves and for electrical myocardial stimulation can involve any suitable technology for producing stimulation pulses of a frequency of between 0 and 100 Hz and an individual pulse duration of between 0 and 10 ms. The pulses can be single-phase or bi-phase.

Nerve stimulation is typically implemented at 20 Hz with a pulse duration of between 0.1 and 4 ms. When the situation involves sinus tachycardia or atrial tachycardia, short bursts (typically of a duration of between 10 and 50 ms) of high-frequency individual stimuli are delivered directly after atrial depolarization (P-wave) in order to avoid atrial myocardial depolarization in particular in the event of parasympathetic stimulation in the right atrium of the coronary sinus. When atrial fibrillation is involved parasympathetic stimulation can be effected in the right atrium and the coronary sinus continuously or in short bursts which are delivered during the R-blip (ventricular depolarization).

The electrodes for detecting the atrial/ventricular frequency were disposed in the atrium/ventricle and are connected to an adjustable signal amplifier which boosts the detected signal to varying degrees, depending on the respective signal magnitude. The band pass properties of the filter of that amplifier are optimized for the detection of atrium/ventricle depolarization phenomena. The mode of operation of the amplifier/filter can correspond to that of known atrium/ventricle pacemakers.

Figure 2A:
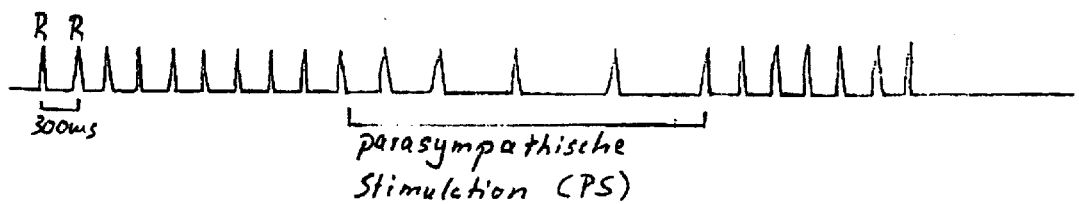
Figure 2B:
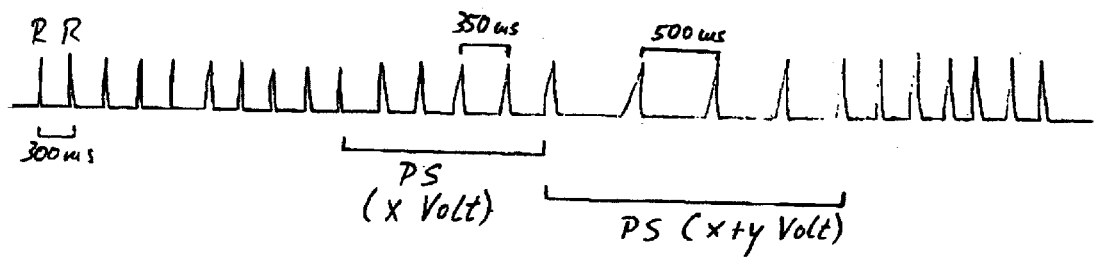
Figure 2C:
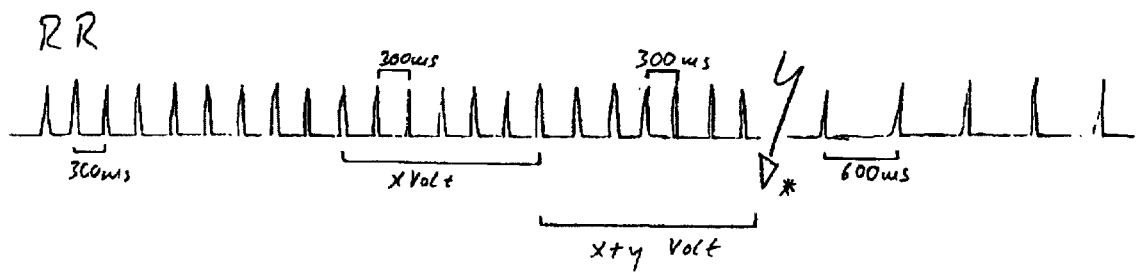
Figure 3:
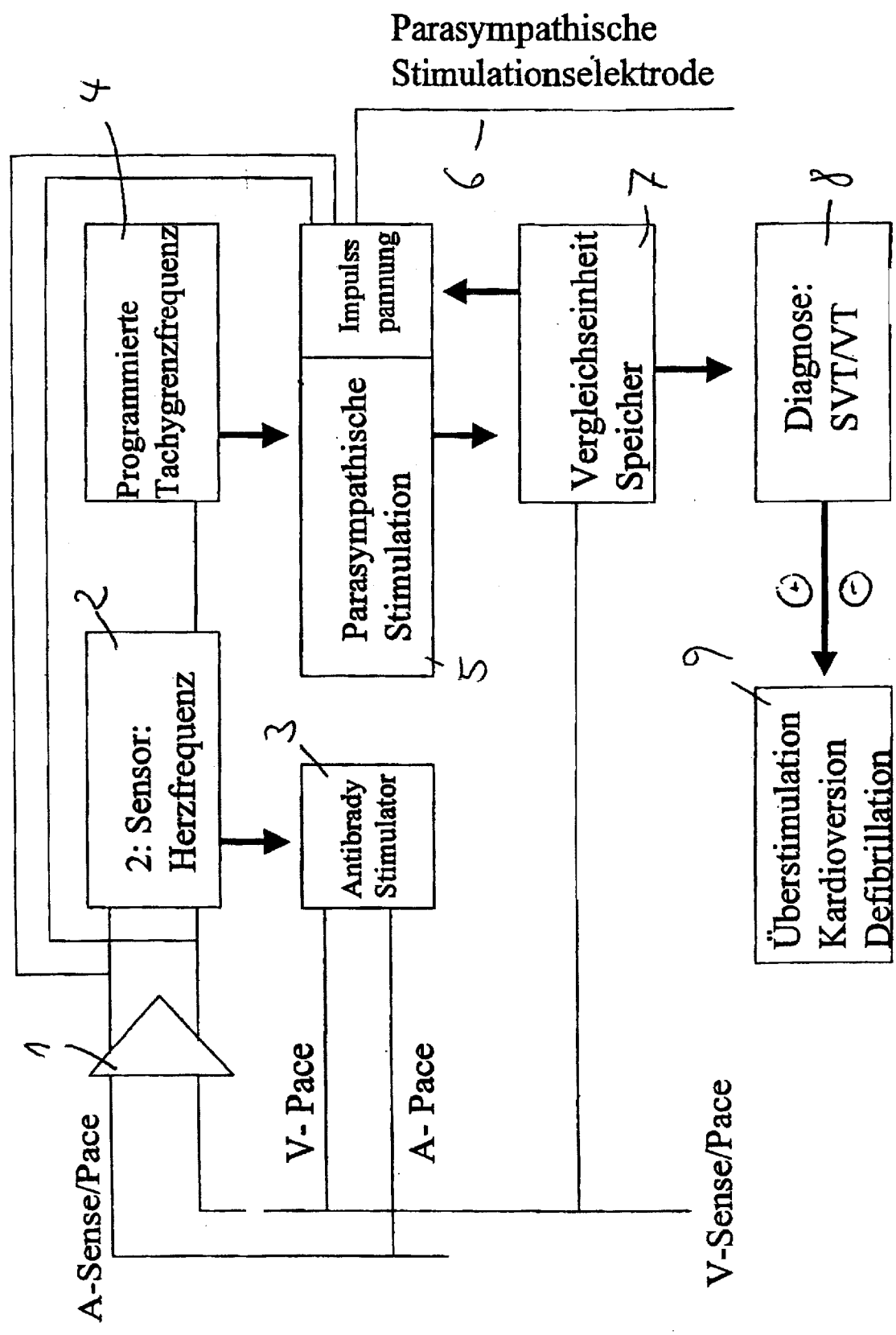

An advantageous embodiment of the invention is described in greater detail hereinafter with reference to the drawings in which:

FIGS. 1A and B show various time diagrams of a simulated electrode upon the occurrence of tachycardias;

FIGS. 2A to C show various time diagrams relating to the parasympathetic stimulation in time relationship with different tachycardias; and FIG. 3 shows a block circuit diagram of the implantable device for distinguishing supraventricular and ventricular tachycardias.

The time diagram shown in FIG. 1A illustrates an example of an intravascular parasympathetic stimulation in a situation involving atrial fibrillation. The stimulation frequency is 20 Hz, with a pulse duration of 3 ms. The respectively shortest and longest R-R intervals during atrial fibrillation are identified. With an increasing stimulation voltage from 3 to 5 volts (corresponding to an output voltage of 15–25 volts), an increasing reduction in the rate of ventricle frequency occurred. With a stimulation voltage of 5 V (table Q) an atrioventricular block grade III was achieved, which resulted in the onset of a ventricular substitute rhythm.

FIG. 1B illustrates an example of an intravascular parasympathetic stimulation with ventricular tachycardia with a cycle length of 260 ms (about 220 beats/minute). The parasympathetic stimulation frequency was 20 Hz with a pulse duration of 3 ms. A slowing of the ventricle frequency occurs during parasympathetic stimulation.

FIG. 2A shows a simulated electrocardiogram of an electrode placed in the ventricle of the heart, with a tachycardia situation (200 beats per minute corresponding to an R-R interval of 300 ms). With a lower tachycardia detection frequency of 150 beats per minute (=R-R interval of 400 ms), the situation involves perception of the tachycardia by the ICD. A brief parasympathetic stimulation is effected as a trial. In that situation, the ventricle frequency is slowed down (the R-R interval is prolonged to 500–600 ms). The comparison unit forms the difference between the cycle length during parasympathetic stimulation and immediately prior to parasympathetic stimulation and ascertains a difference >100 ms. Thereupon diagnosis of a supraventricular tachycardia is implemented and ICD shock therapy is inhibited.

FIG. 2B shows in the simulated electrocardiogram of an electrode placed in the ventricle of the heart a tachycardia (200 beats per minute corresponding to an R-R interval of 300 ms). With a lower tachycardia detection frequency of 150 beats per minute (=R-R interval of 400 ms), the situation involves perception of the tachycardia by the ICD. Brief parasympathetic stimulation is effected by way of trial. In that situation, the ventricle frequency is slowed only to an immaterial degree (prolongation of the R-R interval to 300–350 ms). Therefore, the stimulation voltage of parasympathetic stimulation is doubled, which results in a reduction in the ventricle frequency (prolongation of the R-R interval to 500–600). The comparison unit forms the difference between the cycle length during parasympathetic and immediately prior to parasympathetic stimulation and ascertains a difference >100 ms. Thereupon diagnosis of a supraventricular tachycardia is implemented and ICD shock therapy is inhibited.

In a corresponding manner, as shown in FIG. 2C, a simulated electrocardiogram of an electrode placed in the ventricle of the heart involves a tachycardia (200 beats per minute corresponding to an R-R interval of 300 ms). With a lower tachycardia detection frequency of 150 beats per minute (=R-R interval of 400 ms), the situation involves perception of the tachycardia by the ICD. A brief parasympathetic stimulation is effected by way of trial. The ventricle frequency is not slowed down in that situation. Therefore, the stimulation voltage of parasympathetic stimulation is doubled, which however also does not result in a reduction in the ventricle frequency. The comparison unit forms the difference between the cycle length during parasympathetic stimulation and immediately prior to parasympathetic stimulation and ascertains a difference <100 ms. Thereupon diagnosis of a ventricular tachycardia is implemented and ICD shock therapy is triggered, which results in termination of the ventricular tachycardia.

FIG. 3 shows the block circuit diagram of the implantable device for distinguishing supraventricular and ventricular tachycardia. In the illustrated implanted device, a preamplifier 1 is connected by way of suitable electrodes to the atrium and ventricle. In a situation involving the presence of bradycardia, a sensor 2 for the heart rate controls a conventional pacemaker portion 3 (anti-bradycardia stimulator) for the delivery of stimulation pulses. In addition, connected on the output side of the heart rate sensor 2 is a discriminator 4 for a pre-programmed tachycardia limit frequency. When the programmed limit frequency is exceeded, a control unit for parasympathetic stimulation 5 outputs a corresponding pulse voltage to the parasympathetic stimulation electrode 6. At the same time, a comparison unit 7 is activated, which compares the heart rate which occurs upon parasympathetic stimulation to a predetermined value. If thereupon the heart rate does not slow down, the control signal produced by the comparison unit 7 is transmitted by an inhibition unit 8 to an over-stimulation/cardioversion/defibrillation unit 9 and the corresponding defibrillation procedure is initiated. If in contrast, in the parasympathetic stimulation situation, the natural heart rate is reduced by more than a predetermined minimum amount, defibrillation is prevented. To enhance the level of certainty in respect of the decision, in the last-mentioned case the stimulation amplitude can be implemented by further switching means (not shown), with a stimulation voltage which is also additionally increased. Defibrillation is executed only when the natural heart rate does not change even at the increased (doubled) voltage.

What is claimed is:

1. An implantable device for diagnosing and distinguishing supraventricular and ventricular tachycardias, comprising:

electrodes for the electrical stimulation of parasympathetic nerves which innervate the atrioventricular and/or sinus node;

electrodes for the electrical stimulation of the atria and ventricles and/or for ventricular cardioversion/defibrillation;

a device for producing electrical parasympathetic stimulation pulses which are passed to the electrodes;

a detector for detecting the atrial and/or ventricular rate, by ascertaining a time interval between atrial and/or ventricular depolarization;

a device for programming a frequency limit above which a rate of the ventricles is recognized as tachycardia;

a device to start parasympathetic stimulation by sending a stimulation signal to the parasympathetic pulse producing device as long as the detector detects a ventricular rate above the tachycardia frequency limit;

a comparison device, activated in the presence of a stimulation signal, for comparing a heart rate measured by the detector during parasympathetic stimulation to the heart rate prior to or without parasympathetic stimulation and/or to the frequency limit, the comparison device delivering an output signal of a first type when the heart rate does not fall below a comparison value by more than a predetermined amount and delivering an output signal of a second type when the heart rate falls below the comparison value by more than the predetermined amount, and an inhibition unit that responds to the output signal from the comparison device by initiating ventricular myocardial over-stimulation therapy and/or cardioversion/defibrillation therapy when the output signal of the first type is present and inhibiting ventricular myocardial over-stimulation therapy and/or cardioversion/defibrillation therepy when the output signal of the second type is present.

2. The device of claim 1 wherein the parasympathetic stimulation pulses are delivered over a defined period of time continuously.

3. The device of claim 1, further comprising:
a stimulation unit for atrial and/or ventricular electrical myocardial stimulation.

4. The device of claim 3, wherein the parasympathetic stimulation occurs at a frequency of about 20 Hz with a pulse duration between 0.1 and 4 ms.

5. The device of claim 4, wherein the parasympathetic stimulation occurs in steps which increase in a stage-wise manner.

6. The device of claim 1, wherein the parasympathetic stimulation occurs at a frequency of about 20 Hz with a pulse duration of between 0.1 and 4 ms.

7. The device of claim 6, wherein the parasympathetic stimulation occurs in steps which increase in a stage-wise manner.

8. The device of claim 1, wherein the parasympathetic stimulation occurs in steps which increase in a stage-wise manner.

9. The device as set forth in claim 1 wherein the parasympathetic stimulation pulses are delivered over a defined period of time in short pulse trains.

10. The device of claim 9, wherein the parasympathetic stimulation pulse trains are delivered in synchronized relationship with atrial or ventricular depolarization.

11. The device of claim 10, wherein the parasympathetic stimulation pulse trains are synchronized by a different time delay relative to a measured atrial/ventricular heart contraction.

12. The device of claim 11, further comprising a stimulation unit for atrial and/or ventricular electrical myocardial stimulation.

13. The device of claim 12, wherein the parasympathetic stimulation occurs at a frequency of about 20 Hz with a pulse duration of between 0.1 and 4 ms.

14. The device of claim 13, wherein the parasympathetic stimulation occurs in steps which increase in a stage-wise manner.

15. The device of claim 8, wherein the parasympathetic stimulation pulse trains are delivered asynchronously.

16. The device of claim 15, further comprising a stimulation unit for atrial and/or ventricular electrical myocardial stimulation.

17. The device of claim 16, wherein the parasympathetic stimulation occurs at a frequency of about 20 Hz with a pulse duration of between 0.1 and 4 ms.

18. The device of claim 17, wherein the parasympathetic stimulation occurs in steps which increase in a stage-wise manner.

19. The device of claim 1, further comprising a stimulation unit for cardioversion/defibrillation.

* * * * *